United States Patent
Hoffmann et al.

(10) Patent No.: US 7,759,347 B2
(45) Date of Patent: Jul. 20, 2010

(54) 2-BENZYLAMINODIHYDROPTERIDINONES, PROCESS FOR THEIR MANUFACTURE AND USE THEREOF AS MEDICAMENTS

(75) Inventors: Matthias Hoffmann, Mittelbiberach (DE); Matthias Grauert, Biberach (DE); Thorsten Lehmann-Lintz, Ochsenhausen (DE); Martin Steegmaier, Vienna (AT); Flavio Solca, Vienna (AT); Norbert Redemann, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/357,731

(22) Filed: Jan. 22, 2009

(65) Prior Publication Data
US 2009/0124628 A1 May 14, 2009

Related U.S. Application Data

(63) Continuation of application No. 11/157,883, filed on Jun. 21, 2005, now abandoned.

(30) Foreign Application Priority Data

Jun. 21, 2004 (DE) .................. 10 2004 029 784

(51) Int. Cl.
*A01N 43/58* (2006.01)
*A01N 43/60* (2006.01)
*A61K 31/50* (2006.01)
*A61K 31/495* (2006.01)
*C07D 475/00* (2006.01)

(52) U.S. Cl. .................................. 514/249; 544/258
(58) Field of Classification Search ............... None
See application file for complete search history.

(56) References Cited

U.S. PATENT DOCUMENTS

| | | | |
|---|---|---|---|
| 4,957,922 A | 9/1990 | Lammens et al. |
| 5,167,949 A | 12/1992 | Ferrand et al. |
| 5,424,311 A | 6/1995 | Billhardt-Troughton et al. |
| 5,698,556 A | 12/1997 | Chan |
| 6,096,924 A | 8/2000 | Studer et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,700,769 B2 | 4/2010 | Grauert et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |
| 2007/0213529 A1 | 9/2007 | Duran et al. |

(Continued)

FOREIGN PATENT DOCUMENTS

CA 2458699 A1 3/2003

(Continued)

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray
(74) *Attorney, Agent, or Firm*—Michael P. Morris; Mary-Ellen M. Devlin; Anthony P. Bottino

(57) ABSTRACT

The present invention relates to new 2-benzylaminodihydropteridinones of general formula (I)

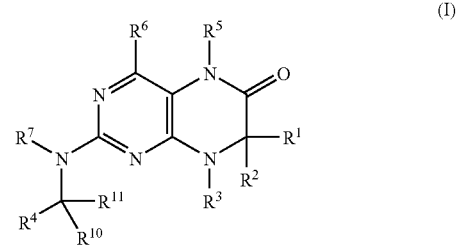

wherein the groups $R^1$ to $R^7$, $R^{10}$ and $R^{11}$ have the meanings given in the claims and specification, the isomers thereof, methods of preparing these dihydropteridinones and their use as medicaments.

8 Claims, No Drawings

U.S. PATENT DOCUMENTS

| | | | |
|---|---|---|---|
| 2007/0213530 | A1 | 9/2007 | Duran et al. |
| 2007/0213531 | A1 | 9/2007 | Duran et al. |
| 2007/0213534 | A1 | 9/2007 | Duran et al. |
| 2007/0219369 | A1 | 9/2007 | Duran et al. |
| 2008/0108812 | A1 | 5/2008 | Grauert et al. |
| 2008/0113992 | A1 | 5/2008 | Grauert et al. |
| 2008/0171747 | A1 | 7/2008 | Hoffman et al. |
| 2008/0177066 | A1 | 7/2008 | Linz et al. |
| 2008/0194818 | A1 | 8/2008 | Grauert et al. |
| 2008/0221099 | A1 | 9/2008 | Munzert et al. |
| 2008/0293944 | A1 | 11/2008 | Hoffmann et al. |
| 2008/0319190 | A1 | 12/2008 | Grauert et al. |
| 2008/0319192 | A1 | 12/2008 | Grauert et al. |
| 2008/0319193 | A1 | 12/2008 | Grauert et al. |
| 2009/0018333 | A1 | 1/2009 | Grauert et al. |
| 2009/0030004 | A1 | 1/2009 | Linz et al. |
| 2009/0124628 | A1 | 5/2009 | Hoffmann et al. |
| 2009/0143379 | A1 | 6/2009 | Mohr et al. |
| 2009/0238828 | A1 | 9/2009 | Munzert et al. |
| 2009/0280115 | A1 | 11/2009 | Maier et al. |
| 2009/0298840 | A1 | 12/2009 | Linz et al. |

FOREIGN PATENT DOCUMENTS

| | | | |
|---|---|---|---|
| CA | 2517020 | A1 | 9/2004 |
| CA | 2517010 | A1 | 11/2004 |
| CA | 2576290 | A1 | 2/2006 |
| EP | 143478 | A1 | 6/1985 |
| EP | 347146 | A2 | 12/1989 |
| EP | 399856 | A1 | 11/1990 |
| EP | 429149 | A1 | 5/1991 |
| ES | 2287583 | | 12/2007 |
| WO | 9609045 | A1 | 3/1996 |
| WO | 9634867 | A1 | 11/1996 |
| WO | 9636597 | A1 | 11/1996 |
| WO | 9811893 | A1 | 3/1998 |
| WO | 0119825 | A1 | 3/2001 |
| WO | 0170741 | A1 | 9/2001 |
| WO | 0178732 | A1 | 10/2001 |
| WO | 02057261 | A2 | 7/2002 |
| WO | 02076954 | A1 | 10/2002 |
| WO | 02076985 | A1 | 10/2002 |
| WO | 03020722 | A1 | 3/2003 |
| WO | 03093249 | A1 | 11/2003 |
| WO | 2004014899 | A1 | 2/2004 |
| WO | 2004076454 | A1 | 9/2004 |
| WO | 2004093848 | A2 | 11/2004 |
| WO | 2005067935 | A1 | 7/2005 |
| WO | 2006/018182 | A1 | 2/2006 |
| WO | 2006/018221 | A1 | 2/2006 |
| WO | 2006018185 | A2 | 2/2006 |
| WO | 2006018220 | A2 | 2/2006 |
| WO | 2006018221 | A1 | 2/2006 |
| WO | 2006021378 | A1 | 3/2006 |
| WO | 2007090844 | A1 | 8/2007 |
| WO | 2009019205 | A1 | 2/2009 |

OTHER PUBLICATIONS

Vippagunta et. al. Advanced Drug Delivery Reviews 48 (2001) 3-26.*

Wolf, Donald E., et al., "The Structure of Rhizopterin". J Am. Chem. Soc., Bd. 69, 1947, pp. 2753-2759, XP002352205.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Webster's Comprehensive Dictionary, 1996, pp. 1013-1014.

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Dipolar aprotic solvent. Exhibit A, IUPAC Compendium of Chemical Terminology, 2nd Edition, 1997.

Doerwald, F.Z. "Side reactions in organice synthesis". 2005.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP—2246920.

Ghandi, L., et al., "An Open-Label Phase II Trial of the PLK Inhibitor BI 2536 in Patients with Sensitive Relapse Small Cell Lung Cancer". ASCO Meeting 2009.

Goodman-Gilman's "The Pharmacological Basis of Therapeutics". Ninth edition, 1996, pp. 1225-1271.

ISR-01-1725-EP2005-006404.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Leukemia & Lymphoma Society—Disease Information-Lymphoma. www.leukemia-lymphoma.org/all_page?item_id-7030, downloaded Mar. 26, 2009.

Leukemia & Lymphoma Society—Disease Information. www.leukemia-lymphoma.org/all_page?item_id-7026, downloaded Mar. 26, 2009.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

Merck Manual of Medical Information—Home Edition, Section 17. "Parasitic Infections". Chapter 184, 2003.

Mito, K., et al., "Expression of polo-like kinase (PLK1) in non-Hodgkin's lymphomas". NCBI, PubMed, 2005, Leuk. Lymphoma, 46(2), pp. 251-231.

Nagao, K. et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

National Kidney Foundation: Chronic Kidney Disease (CKD). www.kidney.org/kidneydisease/ckd/index.cfm, downloaded Mar. 26, 2009.

Norman, P. "PDE4 inhibitors". 1999, Ashley Publications Ltd., pp. 1101-1118.

Office Action mailed Dec. 10, 2003 for U.S. Appl. No. 10/226,710, filed Aug. 23, 2002.

Office Action mailed Apr. 28, 2004 for U.S. Appl. No. 10/374,876, filed Feb. 26, 2003.

Ohio Dept of Health, "Brain and Other Central Nervous System Cancer in Ohio, 1997-2001". Sep. 2004, pp. 1-4.

Organic Chemistry, Grupo Editorial Iberoamerica, Section 13, 3, pp. 301-302, 1983 (best copy available in Spanish).

Rylander, P.N. "Hydrgenation Methods". 1985, Chapter 13.

Rylander, P.N. "Hydrgenation Methods". 1985, Chapters 3, 4.

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Snyder, J. S. et al., "Common bacteria whose susceptibility to antimicrobials is no longer predictable". NCBI, PubMed, 2000, J. Med. Liban, 48, pp. 208-214.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.

Takai, N. et al., "Polo-like kinases (PLKs) and cancer". Oncogene , 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Chen, J.X. et al., "Parallel differentiated recognition of ketones and acetals". Angewandte Chemie Int. Ed, vol. 37, Issue 1/2, p. 91-93, 1998.

Jamieson, C. et al., "Application of ReactArray Robotics and Design of Experiments Techniques in Optimisation of Supported Reagent Chemistry". Org. Proc. Res. & Dev., 2002, 6, p. 823-825.

Mayer, SF, et al., "Enzyme-initiated domino (cascase) reactions". Chem. Soc. Rev, 2001, p. 332-339.

Science, vol. 310, Oct. 21, 2005, p. 409, Chemistry: One After Another.

Turner, S., "The Design of Organic Syntheses". Elsevier, 1976, pp. 10 and 149.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7, 1993, pp. 514-518.

Wikipedia. "Melting Point", Jan. 17, 2007. http://en.wikipedia.org/wiki/Melting_point.

Ahmed, N. "Polo-like kinase (Plk) 1: a novel target for the treatment of prostate cancer". The FASEB Journal. 2004, 18:5-7. Dept of Dermatology, Univ. Wisconsin, pp. 5-7.

Giron, G. "Thermal analysis and calorimetric methods in the characterization of plymorphs and solvates". Thermochimica Acta 248, 1995, pp. 1-59.

Kimball, S.D. et al., "Cell cycle kinases and checkpoint regulation in cancer". Annual Reports in Medicinal Chemistry, 36, Chapter 14, Copyright 2001, pp. 139-148.

Souillac, P. et al., "Characterization of delivery systems, differential scanning calorimetry". (In Encyclopedia of Controlled Drug Delivery). 1999. John Wiley & Sons. pp. 212-227.

\* cited by examiner

2-BENZYLAMINODIHYDROPTERIDINONES, PROCESS FOR THEIR MANUFACTURE AND USE THEREOF AS MEDICAMENTS

CROSS-REFERENCE TO RELATED APPLICATIONS

This is a continuation application and claims the benefit of U.S. patent application Ser. No. 11/157,883 filed Jun. 21, 2005, the entirety of which is incorporated herein by reference.

The present invention relates to new 2-benzylaminodihydropteridinones of general formula (I)

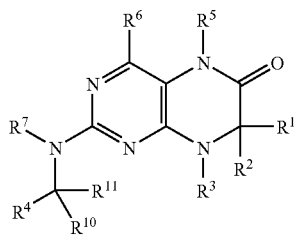

wherein the groups $R^1$ to $R^7$, $R^{10}$ and $R^{11}$ have the meanings given in the claims and specification, the isomers thereof, processes for preparing these dihydropteridinones and their use as medicaments.

BACKGROUND TO THE INVENTION

Pteridinone derivatives are known from the prior art as active substances with an antiproliferative activity. WO 01/019825 and WO 03/020722 describe the use of pteridinone derivatives for the treatment of tumoral diseases.

Tumour cells wholly or partly elude regulation and control by the body and are characterised by uncontrolled growth. This is based on the one hand on the loss of control proteins, such as e.g. Rb, p16, p21 and p53 and also on the activation of so-called accelerators of the cell cycle, the cyclin-dependent kinases (CDK's).

In addition, the protein kinase Aurora B has been described as having an essential function during entry into mitosis. Aurora B phosphorylates histone H3 at Ser10 and thus initiates chromosome condensation (Hsu et al. 2000, *Cell* 102:279-91). A specific cell cycle arrest in the G2/M phase may however also be triggered e.g. by the inhibition of specific phosphatases such as e.g. Cdc25C (Russell and Nurse 1986, *Cell* 45:145-53). Yeasts with a defective Cdc25 gene arrest in the G2 phase, while overexpression of Cdc25 leads to premature entry into the mitosis phase (Russell and Nurse 1987, *Cell* 49:559-67). Moreover, an arrest in the G2/M phase may also be triggered by the inhibition of certain motor proteins, the so-called kinesins such as e.g. Eg5 (Mayer et al. 1999, *Science* 286:971-4), or by agents which stabilise or destabilise microtubules (e.g. colchicin, taxol, etoposide, vinblastin, vincristine) (Schiff and Horwitz 1980, *Proc Nat Acad Sci USA* 77:1561-5).

In addition to the cyclin-dependent and Aurora kinases the so-called polo-like kinases, a small family of serine/threonine kinases, play an important part in the regulation of the eukaryotic cell cycle. Hitherto, the polo-like kinases PLK-1, PLK-2, PLK-3 and PLK-4 have been described in the literature. PLK-1 in particular has been shown to play a central part in the regulation of the mitosis phase. PLK-1 is responsible for the maturation of the centrosomes, for the activation of phosphatase Cdc25C, and for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest in the mitosis phase (Lane and Nigg 1996, *J Cell Biol.* 135:1701-13). Overexpression of PLK-1 has been demonstrated for various types of tumour, such as non-small-cell lung cancer, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also constitutes an interesting approach to therapeutic intervention in proliferative diseases (Liu and Erikson 2003, *Proc Nat Acad Sci USA* 100:5789-5794).

The resistance of many types of tumours calls for the development of new pharmaceutical compositions for combating tumours.

The aim of the present invention is to provide new compounds having an antiproliferative activity.

DETAILED DESCRIPTION OF THE INVENTION

Surprisingly it has been found that compounds of general formula (I) wherein the groups $R^1$ to $R^7$, $R^{10}$ and $R^{11}$ have the meanings given hereinafter act as inhibitors of specific cell cycle kinases particularly the polo-like kinases. The compounds named have an antiproliferative activity, in that they arrest cells in the mitosis phase of the cell cycle before programmed cell death is initiated in the arrested cells. Thus, the compounds according to the invention may be used for example to treat diseases connected with the activity of specific cell cycle kinases and characterised by excessive or abnormal cell proliferation.

The present invention therefore relates to compounds of general formula (I)

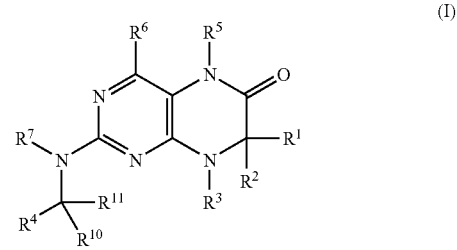

wherein $R^1$, $R^2$ which may be identical or different, denote a group selected from among optionally substituted $C_1$-$C_{10}$-alkyl, $C_2$-$C_{10}$-alkenyl, $C_2$-$C_{10}$-alkynyl, aryl, heteroaryl, $C_3$-$C_8$-cycloalkyl, $C_3$-$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl, and —$NR^8$-heterocycloalkyl, or a group selected from among hydrogen, halogen, $COXR^8$, $CON(R^8)_2$, $COR^8$ and $XR^8$, or $R^1$ and $R^2$ together denote a 2- to 5-membered alkyl bridge which may contain 1 to 2 heteroatoms, $R^3$ denotes hydrogen or a group selected from among optionally substituted $C_1$-$C_{12}$-alkyl, $C_2$-$C_{12}$-alkenyl, $C_2$-$C_{12}$-alkynyl, aryl, heteroaryl, $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl or $R^1$ and $R^3$ or $R^2$ and $R^3$ together denote a saturated or unsaturated $C_3$-$C_4$-alkyl bridge which may contain 1 to 2 heteroatoms, $R^4$ denotes optionally substituted aryl or heteroaryl, $R^5$ denotes a group selected from among hydrogen, CHO, XH, —X—$C_1$-$C_2$-alkyl and an optionally substituted $C_1$-$C_3$-alkyl group, $R^6$ denotes a group selected from among hydrogen, $NH_2$, XH, halogen and a $C_1$-$C_3$-alkyl group optionally substituted by one or more halogen atoms, $R^7$ denotes hydrogen or —CO—$C_1$-$C_4$-alkyl, —CO—NH—$C_1$-$C_4$-alkyl, —CO—X—$C_1$-$C_4$-alkyl, and X in each case independently of one another denote O or S, $R^8$ in each case independently of one another denote hydrogen or a group selected from among optionally substituted $C_1$-$C_4$-alkyl, $C_2$-$C_4$-alkenyl, $C_2$-$C_4$-alkynyl, benzyl and phenyl, $R^{10}$ and $R^{11}$ in each case independently of one another denote hydrogen or a group selected from among optionally substituted $C_1$-$C_4$-alkyl, or $R^{10}$ and $R^{11}$ together denote a 2-5 membered alkyl bridge, optionally in the form of the tautomers, racemates, enantiomers, diastereomers and mixtures thereof, and optionally the pharmacologically acceptable acid addition salts, solvates or hydrates thereof.

Preferred are compounds of formula (I), wherein $R^1$ to $R^4$ have the meanings specified, $R^5$ denotes methyl, and $R^6$ and $R^7$ denote hydrogen, $R^{10}$ and $R^{11}$ in each case independently of one another denote hydrogen or methyl, or $R^{10}$ and $R^{11}$ together denote cyclopropyl.

Also preferred are compounds of formula (I), wherein $R^3$ to $R^7$, $R^{10}$ and $R^{11}$ have the meanings given above and $R^1$, $R^2$ which may be identical or different denote hydrogen or a group selected from among optionally substituted $C_1$-$C_6$-alkyl, $C_2$-$C_6$-alkenyl, and $C_2$-$C_6$-alkynyl, or $R^1$ and $R^2$ together denote a 2- to 5-membered alkyl bridge.

Particularly preferred are compounds of formula (I), wherein $R^1$, $R^3$, $R^4$ to $R^7$, $R^{10}$ and $R^{11}$ have the meanings given above, and $R^3$ is hydrogen or contains a group, selected from among optionally substituted $C_1$-$C_{12}$-alkyl, $C_2$-$C_{12}$-alkenyl, $C_2$-$C_{12}$-alkynyl and $C_6$-$C_{14}$-aryl, or a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl.

Also particularly preferred are compounds of formula (I), wherein $R^1$ to $R^3$, $R^5$ to $R^7$, $R^{10}$ and $R^{11}$ have the meanings given above, and $R^4$ denotes a group of general formula

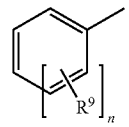

$R^9$ which may be identical or different, denotes a group selected from among optionally substituted $C_1$-$C_6$-alkyl, $C_2$-$C_6$-alkenyl, $C_2$-$C_6$-alkynyl, —O—$C_1$-$C_6$-alkyl, —O—$C_2$-$C_6$-alkenyl, —O—$C_2$-$C_6$-alkynyl, $C_3$-$C_6$-heterocycloalkyl, $C_3$-$C_6$-cycloalkyl, aryl, heteroaryl, —O-aryl, —O-heteroaryl, —O-cycloalkyl, and —O-heterocycloalkyl or a group selected from among hydrogen, —$CONH_2$, —$COOR^8$—$OCON(R^8)_2$, —$N(R^8)_2$, —$NHCOR^8$—NH-$CON(R^8)_2$, —$NO_2$, $CF_3$, halogen, —O—$C_1$-$C_6$-alkyl-$Q^1$, —$CONR^8$—$C_1$-$C_{10}$-alkyl-$Q^1$, —$CONR^8$—$C_2$-$C_{10}$-alkenyl-$Q^1$, —$CONR^8$-$Q^2$, halogen, OH, —$SO_2R^8$, —$SO_2N(R^8)_2$, —$COR^8$—$COOR^8$, —$N(R^8)_2$, —$NHCOR^8$, —$CONR^8OC_1$-$C_{1-10}$-alkyl-$Q^1$ and $CONR^8O$-$Q^2$, $R^8$ in each case independently of one another denotes hydrogen or a group selected from among optionally substituted $C_1$-$C_4$-alkyl, $C_2$-$C_4$-alkenyl, $C_2$-$C_4$-alkynyl and phenyl, $Q^1$ denotes hydrogen, —$NHCOR^8$, or a group selected from among an optionally substituted —NH-aryl, —NH-heteroaryl, aryl, heteroaryl, $C_3$-$C_8$-cycloalkyl and heterocycloalkyl group, $Q^2$ denotes hydrogen or a group selected from among an optionally substituted aryl, heteroaryl and $C_3$-$C_8$-cycloalkyl group, and n denotes 0, 1, 2, 3, 4 or 5.

Particularly preferred are compounds of formula (I), wherein $Q^1$, $Q^2$, n, $R^4$ to $R^9$ have the meanings given above, $R^1$, $R^2$ which may be identical or different, denote hydrogen or a group selected from among methyl, ethyl, propyl, allyl and propargyl or $R^1$ and $R^2$ together denote cyclopropyl, $R^3$ denotes hydrogen, or optionally substituted $C_1$-$C_6$-alkyl or optionally substituted and/or bridged $C_3$-$C_{12}$-cycloalkyl, and $R^{10}$ and $R^{11}$ represent hydrogen.

Most preferred are compounds of formula (I), wherein $Q^1$, $Q^2$, n, $R^1$ to $R^4$, $R^6$ to $R^8$, $R^{10}$ and $R^{11}$ have the meanings given above, and $R^9$ which may be identical or different, denote hydrogen or a group selected from among halogen, ($C_1$-$C_6$-alkyl)$_2$N, $CF_3$, $NH_2SO_2$, —CONH—$C_6$-$C_{14}$-aryl, —CONH—$C_1$-$C_4$-alkyl-$C_6$-$C_{14}$-aryl and —O—$C_1$-$C_4$-alkyl.

The invention further relates to compounds of formula (I) for use as pharmaceutical compositions.

Of particular importance according to the invention are compounds of formula (I) for use as pharmaceutical compositions with an antiproliferative activity.

The invention also relates to the use of a compound of formula (I) for preparing a pharmaceutical composition for the treatment and/or prevention of diseases selected from among cancer, bacterial and viral infections, inflammatory and autoimmune diseases, chemotherapy-induced alopecia and mucositis, cardiovascular diseases, nephrological diseases, as well as chronic and acute neurodegenerative diseases, preferably for the treatment of cancer, inflammatory and autoimmune diseases, particularly preferably for the treatment of cancer and inflammatory diseases.

The invention further relates to the use of a compound of formula (I) for preparing a pharmaceutical composition for inhibiting the polo-like kinases, particularly the polo-like kinase PLK-1.

The invention further relates to the use of a compound of formula (I) for preparing a pharmaceutical composition for the treatment and/or prevention of tumour diseases based on the overexpression of the polo-like kinases, particularly the PLK-1 kinases.

The invention further relates to a method for the treatment and/or prevention of diseases selected from among cancer, bacterial and viral infections, inflammatory and autoimmune diseases, chemotherapy-induced alopecia and mucositis, cardiovascular diseases, nephrological diseases, as well as chronic and acute neurodegenerative diseases, preferably for the treatment of cancer, inflammatory and autoimmune diseases, particularly preferably for the treatment of cancer and inflammatory diseases, in which an effective amount of a compound of formula (I) is administered to a patient.

The invention also relates to pharmaceutical preparations, containing as active substance one or more compounds of general formula (I) optionally combined with conventional excipients and/or carriers.

The term alkyl groups, including alkyl groups which are a part of other groups, denotes branched and unbranched alkyl groups with 1 to 12 carbon atoms, preferably 1-6, most preferably 1-4 carbon atoms, such as, for example: methyl, ethyl, propyl, butyl, pentyl, hexyl, heptyl, octyl, nonyl and decyl. Unless otherwise stated, the abovementioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the abovementioned alkyl groups one or more hydrogen atoms may optionally be replaced by other groups. For example these alkyl groups may be substituted by methyl, chlorine or fluorine, preferably fluorine. All the hydrogen atoms of the alkyl group may optionally also be replaced.

The term alkyl bridge, unless otherwise stated, denotes branched and unbranched alkyl groups with 2 to 5 carbon atoms, for example ethylene, propylene, isopropylene, n-butylene, iso-butyl, sec. butyl and tert.-butyl etc. bridges. Ethylene, propylene and butylene bridges are particularly preferred. In the alkyl bridges mentioned 1 to 2 C-atoms may optionally be replaced by one or more heteroatoms selected from among oxygen, nitrogen or sulphur.

The term alkenyl groups (including those which are a part of other groups) denotes branched and unbranched alkylene groups with 2 to 10 carbon atoms, preferably 2-6 carbon atoms, most preferably 2-3 carbon atoms, provided that they have at least one double bond. Examples include: ethenyl, propenyl, butenyl, pentenyl etc. Unless otherwise stated, the abovementioned terms propenyl, butenyl, etc also include all the possible isomeric forms. For example, the term butenyl includes 1-butenyl, 2-butenyl, 1-methyl-1-propenyl, 1-methyl-2-propenyl, 2-methyl-1-propenyl, 2-methyl-2-propenyl and 1-ethyl-1-ethenyl.

In the abovementioned alkenyl groups, unless otherwise stated, one or more hydrogen atoms may optionally be replaced by other groups. For example, these alkenyl groups may be substituted by methyl, chlorine or fluorine, preferably fluorine. All the hydrogen atoms of the alkenyl group may optionally also be replaced.

The term alkynyl groups (including those which are a part of other groups) denotes branched and unbranched alkynyl groups with 2 to 10 carbon atoms, provided that they have at least one triple bond, for example ethynyl, propargyl, butynyl, pentynyl, hexynyl etc., preferably ethynyl or propynyl.

In the abovementioned alkynyl groups, unless otherwise stated, one or more hydrogen atoms may optionally be replaced by other groups. For example, these alkynyl groups may be substituted by methyl, chlorine or fluorine, preferably fluorine. All the hydrogen atoms of the alkynyl group may optionally also be replaced.

The term aryl denotes an aromatic ring system with 6 to 14 carbon atoms, preferably 6 or 10 carbon atoms, preferably phenyl, which, unless otherwise stated, may carry one or more of the following substituents, for example: OH, $NO_2$, CN, OMe, —$OCHF_2$, —$OCF_3$, —$NH_2$, halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —O-methyl or —O-ethyl, or —$CONH_2$.

Examples of heteroaryl groups wherein up to two C atoms are replaced by one or two nitrogen atoms are, for example, pyrrole, pyrazole, imidazole, triazole, pyridine, pyrimidine, while each of the above-mentioned heteroaryl rings may optionally also be anellated to a benzene ring, preferably benzimidazole, and these heterocycles, unless stated to the contrary, may for example carry one or more of the following substituents: F, Cl, Br, OH, OMe, methyl, ethyl, CN, $CONH_2$, $NH_2$, optionally substituted phenyl, optionally substituted heteroaryl, preferably optionally substituted pyridyl.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example: OH, $NO_2$, CN, OMe, —$OCHF_2$, —$OCF_3$, —$NH_2$ or halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —COO-methyl or —COO-ethyl or —$CONH_2$. Particularly preferred substituents of the cycloalkyl groups are ═O, OH, $NH_2$, methyl or F.

Examples of cycloalkenyl groups are cycloalkyl groups with 3-12 carbon atoms which have at least one double bond, for example cyclopropenyl, cyclobutenyl, cyclopentenyl, cyclohexenyl or cycloheptenyl, preferably cyclopropenyl, cyclopentenyl or cyclohexenyl, while each of the abovementioned cycloalkenyl groups may optionally also carry one or more substituents.

"═O" denotes an oxygen atom linked by a double bond.

Examples of heterocycloalkyl groups, unless otherwise stated in the definitions, are 3 to 12 membered, preferably 5-, 6- or 7-membered, saturated or unsaturated heterocycles, which may contain as heteroatoms nitrogen, oxygen or sulphur, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, pyrazolidine, preferably morpholine, pyrrolidine, piperidine or piperazine, while the heterocyclic group may optionally carry substituents, for example $C_1$-$C_4$-alkyl, preferably methyl, ethyl or propyl.

Examples of polycycloalkyl groups are optionally substituted, bi-, tri-, tetra- or pentacyclic cycloalkyl groups, for example pinane, 2,2,2-octane, 2,2,1-heptane or adamantane. Examples of polycycloalkenyl groups are optionally bridged and/or substituted, 8-membered bi-, tri-, tetra- or pentacyclic cycloalkenyl groups, preferably bicycloalkenyl or tricycloalkenyl groups, if they contain at least one double bond, for example norbornene.

Examples of spiroalkyl groups are optionally substituted spirocyclic $C_5$-$C_{12}$ alkyl groups.

The term halogen generally denotes fluorine, chlorine, bromine or iodine, preferably fluorine, chlorine or bromine, particularly preferably chlorine.

The compounds according to the invention may be present in the form of the individual optical isomers, mixtures of the individual enantiomers, diastereomers or racemates, in the form of the tautomers, in the form of the solvates, preferably in the form of the hydrates thereof and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

The substituent $R^1$ may be a group selected from among optionally substituted $C_1$-$C_{10}$-alkyl, preferably $C_1$-$C_4$-alkyl, particularly preferably methyl, ethyl or propyl, $C_2$-$C_{10}$-alkenyl, preferably allyl, $C_2$-$C_{10}$-alkynyl, preferably propargyl, aryl, heteroaryl, $C_3$-$C_8$-cycloalkyl, $C_3$-$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl, and —$NR^8$-heterocycloalkyl, or a group selected from among hydrogen, halogen, $COXR^8$, $CON(R^8)_2$, $COR^8$ and $XR^8$, preferably hydrogen.

Preferably the substituent $R^1$ denotes ethyl or hydrogen, particularly preferably hydrogen.

The substituent $R^2$ may represent a group selected from among optionally substituted $C_1$-$C_{10}$-alkyl, preferably $C_1$-$C_4$-alkyl, particularly preferably methyl, ethyl or propyl, $C_2$-$C_{10}$-alkenyl, preferably allyl, $C_2$-$C_{10}$-alkynyl, preferably propargyl, aryl, heteroaryl, $C_3$-$C_8$-cycloalkyl, $C_3$-$C_8$-heterocycloalkyl, —X-aryl, —X-heteroaryl, —X-cycloalkyl, —X-heterocycloalkyl, —$NR^8$-aryl, —$NR^8$-heteroaryl, —$NR^8$-cycloalkyl, and —$NR^8$-heterocycloalkyl, or a group selected from among hydrogen, halogen, $COXR^8$, $CON(R^8)_2$, $COR^8$ and $XR^8$, preferably hydrogen.

Preferably the substituent $R^2$ denotes ethyl or hydrogen, particularly preferably ethyl.

The substituents $R^1$ and $R^2$ may together denote a 2- to 5-membered alkyl bridge, preferably a 2-membered alkyl bridge which may contain 1 to 2 heteroatoms, for example oxygen, sulphur or nitrogen, preferably oxygen or nitrogen.

The substituent $R^3$ may denote hydrogen or a group selected from among optionally substituted $C_1$-$C_{12}$-alkyl, preferably $C_1$-$C_6$-alkyl, $C_2$-$C_{12}$-alkenyl, $C_2$-$C_{12}$-alkynyl, aryl, heteroaryl, —$C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl or $R^1$ and $R^3$ or $R^2$ and $R^3$ together denote a saturated or unsaturated $C_3$-$C_4$-alkyl bridge which may contain 1 to 2 heteroatoms.

Preferably the substituent $R_3$ denotes $C_1$-$C_6$-alkyl or —$C_3$-$C_{12}$-cycloalkyl, particularly preferably methyl or cyclopentyl.

The substituent $R^4$ may represent optionally substituted aryl or heteroaryl, preferably a group of general formula

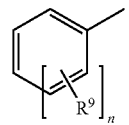

The index n may represent 0, 1, 2, 3, 4 or 5, preferably 1 or 2, particularly preferably 1.

The substituent $R^5$ may represent a group selected from among hydrogen, halogen, CHO, XH, —X—$C_1$-$C_2$-alkyl and an optionally substituted $C_1$-$C_3$-alkyl group, preferably methyl.

Preferably the substituent $R^5$ denotes methyl.

The substituent $R^6$ may represent a group selected from among hydrogen, $NH_2$, XH, halogen and a $C_1$-$C_3$-alkyl group optionally substituted by one or more halogen atoms.

Preferably the substituent $R^6$ denotes hydrogen.

The substituent $R^7$ may represent hydrogen, —CO—X—$C_1$-$C_4$-alkyl, preferably —CO—O-methyl or —CO—O-ethyl, —CO—NH—$C_1$-$C_4$-alkyl, preferably —CO—NH-methyl or —CO—NH-ethyl, or —CO—$C_1$-$C_4$-alkyl, preferably —CO-methyl. Preferably the substituent $R^7$ denotes hydrogen.

X may in each case independently of one another denote oxygen or sulphur, preferably oxygen.

The substituent $R^8$ may in each case independently of one another denote hydrogen or a group selected from among optionally substituted $C_1$-$C_4$-alkyl, preferably methyl or ethyl, $C_2$-$C_4$-alkenyl, $C_2$-$C_4$-alkynyl, benzyl and phenyl. Preferably the substituent $R^8$ denotes methyl, phenyl or benzyl.

The substituent $R^9$ which may be identical or different, may denote a group selected from among optionally substituted $C_1$-$C_6$-alkyl, preferably methyl, ethyl or isopropyl, $C_2$-$C_6$-alkenyl, preferably allyl or homoallyl, $C_2$-$C_6$-alkynyl, preferably propargyl —O—$C_1$-$C_6$-alkyl, preferably —O-methyl or —O-ethyl, —O—$C_2$-$C_6$-alkenyl, —O—$C_2$-$C_6$-alkynyl, $C_3$-$C_6$-heterocycloalkyl, preferably piperazinyl, morpholinyl, pyrrolidinyl or piperidinyl, $C_3$-$C_6$-cycloalkyl, preferably cyclopropyl, cyclopentyl or cyclohexyl, aryl, preferably phenyl, or naphthalenyl, heteroaryl, preferably pyridinyl or pyrimidinyl, —O-aryl, preferably —O-phenyl, O-heteroaryl, preferably O-pyridinyl or O-pyrimidinyl, —O-cycloalkyl, preferably O-cyclopentyl, or O-cyclohexyl, and —O-heterocycloalkyl, preferably —O-morpholinyl, —O-piperidinyl, —O-pyrrolidinyl, or —O-piperazinyl, or a group selected from among hydrogen, —$CONH_2$, —$COOR^8$, —$OCON(R^8)_2$, —$N(R^8)_2$, —$NHCOR^8$, —$NHCON(R^8)_2$, —$NO_2$, $CF_3$, halogen, —O—$C_1$-$C_6$-alkyl-$Q^1$, —$CONR^8$—$C_1$-$C_{10}$-alkyl-$Q^1$, —$CONR^8$—$C_2$-$C_{10}$-alkenyl-$Q^1$, —$CONR^8$-$Q^2$, halogen, OH, —$SO_2R^8$, —$SO_2N(R^8)_2$, —COR⁸, —COOR⁸, —N(R⁸)₂, —NHCOR⁸, —CONR⁸OC₁-C₁₀-alkyl-Q¹ and —CONR⁸O-Q².

Preferably the substituent $R^9$ denotes —CONR⁸-Q² or —CONR⁸OC₁-C₁₀-alkyl-Q¹. The substituents $R^{10}$ and $R^{11}$ may in each case independently of one another denote hydrogen or optionally substituted $C_1$-$C_4$-alkyl, preferably hydrogen or methyl, or $R^{10}$ and $R^{11}$ may together denote a 2-5 membered alkyl bridge, preferably a 2-membered alkyl bridge.

Particularly preferably the substituents $R^{10}$ and $R^{11}$ denote hydrogen.

$Q^1$ may represent hydrogen, —NHCOR⁸ or a group selected from among an optionally substituted —NH-aryl, —NH-heteroaryl, aryl, preferably phenyl, heteroaryl, $C_3$-$C_8$-cycloalkyl and heterocycloalkyl group.

$Q^2$ may represent hydrogen or a group selected from among an optionally substituted aryl, preferably phenyl, heteroaryl and $C_3$-$C_8$-cycloalkyl group.

All the groups mentioned in the definitions of $R^1$ to $R^9$ may optionally be branched and/or substituted.

The compounds of general formula (I) may be prepared by the following method of synthesis, while the substituents of general formulae (A1), (A2) and (I) are as hereinbefore defined. This method is to be understood as illustrating the invention without restricting it to the object thereof.

A compound of formula (A1) is reacted with an optionally substituted benzylamine (A2) to obtain general formula (I). The compounds of formula (A1) may be obtained as described on page 23 of WO 2003/020722. Enantiomerically pure compounds (A1) with respect to the stereochemistry at R1/R2 may also be obtained analogously to the process described therein. The 4-aminomethyl-N-benzylbenzamide used may be obtained e.g. according to the following reference: H. G. Kazmirowski, P. Neuland, H. Landmann, F. Markwardt *Pharmazie* 1967, 22(9), 465-70.

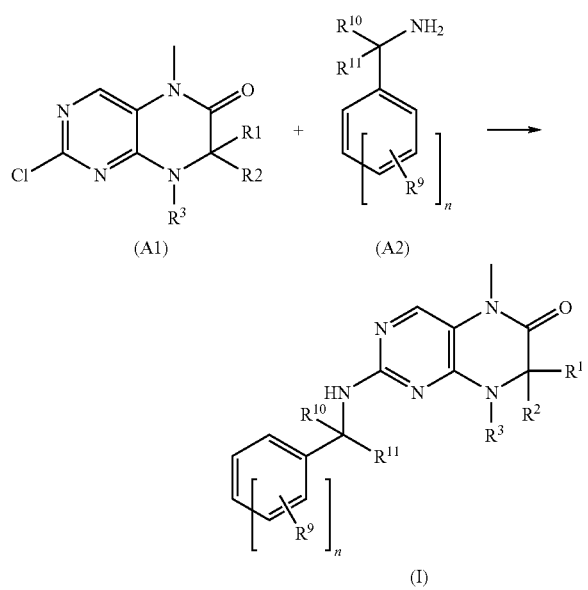

The new compounds of general formula (I) may be prepared analogously to the following Examples.

The following 2-chloro-dihydropteridinones were used in the syntheses:

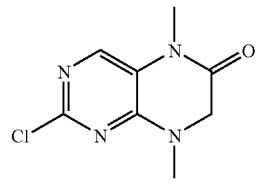

1

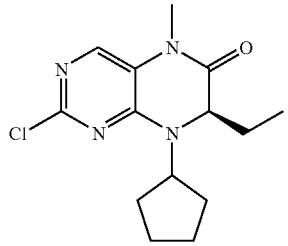

2

EXAMPLE 9

0.5 g 1 was stirred together with 1.15 g 4-aminomethyl-N-benzylbenzamide in 2.5 mL sulpholane for 30 min to 160° C. After the reaction solution had cooled it was diluted with 20 mL methanol and the precipitate formed was filtered off, washed again with methanol and dried. It yielded 470 mg light brown crystals of m.p. 162° C.

EXAMPLE 10

0.2 g 1 was stirred with 0.4 g 4-aminomethylbenzenesulphonamide x HCl and 0.34 mL 30% sodium methoxide solution in 1 mL sulpholane at 160° C. for 2 h. After cooling it was diluted with methanol and ether, filtered off from the precipitate, the mother liquor was evaporated down and the residue was extracted with methylene chloride and 2N hydrochloric acid. A yellow precipitate crystallised out from the methylene chloride phase and this was filtered off and dried. It yielded 40 mg yellow crystals of m.p. 248° C.

EXAMPLE 11

0.1 g 2 was melted together with 168 μL benzylamine without solvent at 160° C. for 1 h and 45 minutes. After cooling the residue was dissolved with a little dichloromethane and methanol and combined with ether. The precipitate formed was filtered off and the mother liquor evaporated down and subjected to chromatography on silica gel. The eluant used was dichloromethane:methanol:aqueous ammonia solution in the ratio 95:5:0.5. Then the fractions containing the product were combined and evaporated down. The residue was dissolved in ethyl acetate, combined with ethereal HCl and petroleum ether and the precipitate was filtered off. It yielded 0.08 g of a light brown hygroscopic solid.

EXAMPLE 12

0.1 g 2 and 95 μL 3-chlorobenzylamine were heated without solvent for 2 h at 160° C. The cooled reaction mixture was digested with methanol and dichloromethane and combined with ether. The precipitate was filtered off and the mother liquor was purified by chromatography as described in Example 11. The product fractions were combined and evaporated down. Then the product was dissolved in acetone, combined with an oxalic acid solution in isopropanol and the precipitate was filtered off and dried. It yielded 72 mg of a white solid, m.p. 171° C.

EXAMPLE 14

0.1 g 2 and 100 µL 3-methoxybenzylamine were heated to 160° C. without solvent for 2 h. The cooled reaction mixture was digested with methanol and dichloromethane and combined with ether. The precipitate was filtered off and the mother liquor was purified by chromatography as described in Example 11. The product fractions were combined and evaporated down. Then the product was dissolved in acetone, combined with an oxalic acid solution in isopropanol and the precipitate was filtered off and dried. It yielded 97 mg of a white solid of m.p. 175° C.

The compounds of general formula (I) listed in Table 1, inter alia, were obtained analogously to the method described above.

TABLE 1

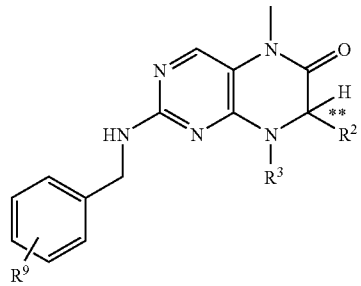

| Example | Config. **H/R2 | $R^2$ | $R^3$ | $R^9$ ortho | $R^9$ meta | $R^9$ para | m.p. |
|---|---|---|---|---|---|---|---|
| 1 | | H | —CH$_3$ | H | H | H | |
| 2 | | H | —CH$_3$ | H | H | Cl | 250° C. |
| 3 | | H | —CH$_3$ | H | —CF$_3$ | H | 206° C. |
| 4 | | H | —CH$_3$ | H | —OCH$_3$ | H | 194° C. |
| 5 | | H | —CH$_3$ | H | H | —OCH$_3$ | 195° C. |
| 6 | | H | —CH$_3$ | H | H | F | 253° C. |
| 7 | | H | —CH$_3$ | —OCH$_3$ | H | H | 194° C. |
| 8 | | H | CH$_3$ | H | H | —N(CH$_3$)$_2$ | 235° C. |
| 9 | | H | —CH$_3$ | H | H | 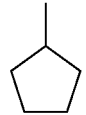 | 162° C. |
| 10 | | H | —CH$_3$ | H | H | —SO$_2$NH$_2$ | 248° C. |
| 12 | R | —CH$_2$CH$_3$ | 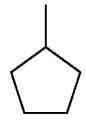 | H | Cl | H | 171° C. |
| 13 | R | —CH$_2$CH$_3$ |  | H | H | Cl | 149° C. |
| 14 | R | —CH$_2$CH$_3$ | 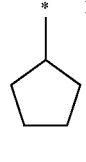 | —OCH$_3$ | H | H | 175° C. |
| 15 | R | —CH$_2$CH$_3$ | * | H | H | H | 144° C. |

TABLE 1-continued

| Example | Config. **H/R2 | R² | R³ | R⁹ ortho | R⁹ meta | R⁹ para | m.p. |
|---|---|---|---|---|---|---|---|
| 16 | R | —CH₂CH₃ | * cyclopentyl | Cl | H | H | 177° C. |
| 17 | R | —CH₂CH₃ | * cyclopentyl | H | H | —OCH₃ | |

*position of bond

As has been found, the compounds of general formula (I) are characterised by their wide range of applications in the therapeutic field. Particular mention should be made of those applications in which the inhibition of specific cell cycle kinases, particularly the inhibiting effect on the proliferation of cultivated human tumour cells but also the proliferation of other cells, such as endothelial cells, for example, plays a part.

As could be demonstrated by DNA staining followed by FACS analysis, the inhibition of proliferation brought about by the compounds according to the invention is mediated by the arrest of the cells, particularly at the G2/M phase of the cell cycle. The cells arrest, depending on the cells used, for a specific length of time in this phase of the cell cycle before programmed cell death is initiated. An arrest in the G2/M phase of the cell cycle is triggered, for example, by the inhibition of specific cell cycle kinases. In view of their biological properties the compounds of general formula I according to the invention, their isomers and their physiologically acceptable salts are suitable for the treatment of diseases characterised by excessive or abnormal cell proliferation.

Such diseases include, for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also suitable for protecting proliferating cells (e.g. hair, intestinal, blood and progenitor cells) from damage to their DNA caused by radiation, UV treatment and/or cytostatic treatment (Davis et al., 2001).

The new compounds may be used for the prevention, short-term or long-term treatment of the abovementioned diseases, also in combination with other active substances used for the same indications, e.g. cytostatics, hormones or antibodies.

The activity of the compounds according to the invention was determined in the PLK1 inhibition assay, in the cytotoxicity test on cultivated human tumour cells and/or in a FACS analysis, for example on HeLaS3 cells. In both test methods, the compounds exhibited a good to very good activity, i.e. for example an $EC_{50}$ value in the HeLaS3 cytotoxicity test of less than 5 µmol/L, generally less than 1 µmol/L and an $IC_{50}$ value in the PLK1 inhibition assay of less than 1 µmol/L.

PLK1 Kinase Assay

Preparation of Enzyme:

Recombinant human PLK1 enzyme attached to GST at its N-terminal end is isolated from Baculovirus-infected insect cells (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 µM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g Na₂HPO₄/l, 0.24 g KH₂PO₄/l). After centrifuging again the pellet is flash-frozen in liquid nitrogen. Then the pellet is quickly thawed and resuspended in ice-cold lysing buffer (50 mM HEPES pH 7.5, 10 mM MgCl₂, 1 mM DTT, 5 µg/ml leupeptin, 5 µg/ml aprotinin, 100 µM NaF, 100 µM PMSF, 10 mM β-glycerolphosphate, 0.1 mM Na₃VO₄, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Assay

The following components are combined in a well of a 96-well round-bottomed dish (Greiner bio-one, PS Microtitre plate No. 650101):

10 µl of the compound to be tested in variable concentrations (e.g. beginning at 300 µM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT 20 µl substrate solution (25 mM MOPS pH=7.0, 15 mM $MgCl_2$, 1 mM DTT, 2.5 mM EGTA, 30 mM β-glycerophosphate, 0.25 mg/ml casein)

20 µl enzyme dilution (1:100 dilution of the enzyme stock in 25 mM MOPS pH=7.0, 15 mM $MgCl_2$, 1 mM DTT)

10 µl ATP solution (45 µM ATP with $1.11 \times 10^6$ Bq/ml gamma-P33-ATP).

The reaction is started by adding the ATP solution and continued for 45 minutes at 30° C. with gentle shaking (650 rpm on an IKA Schuttler MTS2). The reaction is stopped by the addition of 125 µl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 µl scintillation solution (Ready-Safe; Beckmann) per well the plate is sealed shut with sealing tape and the amount of P33 precipitated is measured with the Wallac Betacounter.

The measured data are evaluated using the standard Graphpad software (Levenburg-Marquard Algorhythmus).

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) are cultivated in Ham's F12 Medium (Life Technologies) and 10% foetal calf serum (Life Technologies) and harvested in the log growth phase. Then the HeLa S3 cells are placed in 96-well plates (Costar) at a density of 1000 cells per well and incubated overnight in an incubator (at 37° C. and 5% CO2), while on each plate 6 wells are filled with medium alone (3 wells as the medium control, 3 wells for incubation with reduced AlamarBlue reagent). The active substances are added to the cells in various concentrations (dissolved in DMSO; DMSO final concentration: 0.1%) (in each case as a triple measurement). After 72 hours incubation 20 µl AlamarBlue reagent (AccuMed International) are added to each well, and the cells are incubated for a further 7 hours. As a control, 20 µl reduced AlamarBlue reagent is added to each of 3 wells (AlamarBlue reagent, which is autoclaved for 30 min). After 7 h incubation the colour change of the AlamarBlue reagent in the individual wells is determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity is calculated as a percentage of the control (HeLa S3 cells without inhibitor) and the active substance concentration which inhibits the cell activity by 50% ($IC_{50}$) is derived. The values are calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, 0.4 million HeLa S3 cells were seeded onto a 75 $cm^2$ cell culture flask, and after 24 h either 0.1% DMSO was added as control or the substance was added in various concentrations (in 0.1% DMSO). The cells were incubated for 24 h with the substance or with DMSO before the cells were washed 2× with PBS and then detached with trypsin/EDTA. The cells were centrifuged (1000 rpm, 5 min, 4° C.), and the cell pellet was washed 2× with PBS before the cells were resuspended in 0.1 ml PBS. Then the cells were fixed with 80% ethanol for 16 hours at 4° C. or alternatively for 2 hours at −20° C. The fixed cells were centrifuged (1000 rpm, 5 min, 4° C.), washed with PBS and then centrifuged again. The cell pellet was resuspended in 2 ml 0.25% Triton X-100 in PBS, and incubated on ice for 5 min before 5 ml PBS are added and the mixture is centrifuged again. The cell pellet was resuspended in 350 µl PI staining solution (0.1 mg/ml RNase A (Sigma, No. R-4875), 10 µg/ml prodium iodide (Sigma, No. P-4864) in 1×PBS). The cells were incubated for 20 min in the dark with the staining buffer before being transferred into sample measuring containers for the FACS scan. The DNA measurement was carried out in a Becton Dickinson FACS Analyzer, with an argon laser (500 mW, emission 488 nm), and the DNA Cell Quest Programme (BD). The logarithmic PI fluorescence was determined with a band-pass filter (BP 585/42). The cell populations in the individual cell cycle phases were quantified using the ModFit LT Programme made by Becton Dickinson.

The compounds according to the invention were also tested accordingly on other tumour cells. For example, these compounds are effective on carcinomas of all kinds of tissue (e.g. breast (MCF7); colon (HCT116), head and neck (FaDu), lung (NCI-H460), pancreas (BxPC-3), prostate (DU145)), sarcomas (e.g. SK-UT-1B, Saos-2), leukaemias and lymphomas (e.g. HL-60, Jurkat, THP-1) and other tumours (e.g. melanomas (BRO), gliomas (U-87MG)) and could be used for such indications. This is evidence of the broad applicability of the compounds according to the invention for the treatment of all kinds of tumour types.

The compounds of general formula (I) may be used on their own or in conjunction with other active substances according to the invention, optionally also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of formula (I), (I)

[Structure of compound with substituents $R^1$, $R^2$, $R^3$, $R^4$, $R^5$, $R^6$, $R^7$, $R^{10}$, $R^{11}$]

wherein
$R^1$, $R^2$ which may be identical or different, denote a group selected from among optionally substituted $C_1$-$C_{10}$-alkyl, $C_3$-$C_8$-cycloalkyl and hydrogen,
or
$R^1$ and $R^2$ together denote a 2- to 5-membered alkyl bridge,
$R^3$ denotes hydrogen or a group selected from among optionally substituted $C_1$-$C_{12}$-alkyl and $C_3$-$C_{12}$-cycloalkyl, or
$R^1$ and $R^3$ or $R^2$ and $R^3$ together denote a saturated or unsaturated $C_3$-$C_4$-alkyl bridge which may contain 1 to 2 heteroatoms,
$R^4$ denotes optionally mono-substituted aryl or,
$R^5$ denotes a group selected from among hydrogen, CHO, XH, —X—$C_1$-$C_2$-alkyl and an optionally substituted $C_1$-$C_3$-alkyl group,
$R^6$ denotes a group selected from among hydrogen, $NH_2$, XH, halogen and a $C_1$-$C_3$-alkyl group optionally substituted by one or more halogen atoms,
$R^7$ denotes hydrogen or —CO—$C_1$-$C_4$-alkyl, —CO—NH—$C_1$-$C_4$-alkyl, —CO—X—$C_1$-$C_4$-alkyl, and
X in each case independently of one another denote O or S,
$R^8$ in each case independently of one another denote hydrogen or a group selected from among optionally substituted $C_1$-$C_4$-alkyl, $C_2$-$C_4$-alkenyl, $C_2$-$C_4$-alkynyl, benzyl and phenyl,
$R^{10}$ and $R^{11}$ in each case independently of one another denote hydrogen or a group selected from among optionally substituted $C_1$-$C_4$-alkyl,
or $R^{10}$ and $R^{11}$ together denote a 2-5 membered alkyl bridge,
or the pharmacologically acceptable acid addition salt thereof.

2. The compound according to claim 1,
wherein
$R^1$ to $R^4$ have the meanings specified,
$R^5$ denotes methyl, and
$R^6$ and $R^7$ denote hydrogen,
$R^{10}$ and $R^{11}$ in each case independently of one another denote hydrogen or methyl,
or
$R^{10}$ and $R^{11}$ together denote cyclopropyl.

3. The compound according to claim 2,
wherein
$R^3$ to $R^7$, $R^{10}$ and $R^{11}$ have the meanings specified and
$R^1$, $R^2$ which may be identical or different, denote hydrogen or a group selected from optionally substituted $C_1$-$C_6$-alkyl,
or
$R^1$ and $R^2$ together denote a 2- to 5-membered alkyl bridge.

4. The compound according to claim 1,
wherein
$R^3$ is hydrogen or contains a group selected from among optionally substituted $C_1$-$C_{12}$-alkyl and $C_3$-$C_{12}$-cycloalkyl.

5. The compound according to claim 4,
wherein
$R^1$ to $R^3$, $R^5$ to $R^7$, $R^{10}$ and $R^{11}$ have the meanings specified, and
$R^4$ denotes a group of formula

[Structure showing phenyl ring with $(R^9)_n$ substituent]

$R^9$ which may be identical or different, denotes a group selected from among optionally substituted $C_1$-$C_6$-alkyl, $C_2$-$C_6$-alkenyl, $C_2$-$C_6$-alkynyl, —O—$C_1$-$C_6$-alkyl, —O—$C_2$-$C_6$-alkenyl, —O—$C_2$-$C_6$-alkynyl, $C_3$-$C_6$-heterocycloalkyl, $C_3$-$C_6$-cycloalkyl, aryl, heteroaryl, —O-aryl, —O-heteroaryl, —O-cycloalkyl, and —O-heterocycloalkyl or a group selected from among hydrogen, —$CONH_2$, —$COOR^8$, —$OCON(R^8)_2$, —$N(R^8)_2$, —$NHCOR^8$, —$NHCON(R^8)_2$, —$NO_2$, $CF_3$, halogen, —O—$C_1$-$C_6$-alkyl-$Q^1$, —$CONR^8$—$C_1$-$C_{10}$-alkyl-$Q^1$, —$CONR^8$—$C_2$-$C_{10}$-alkenyl-$Q^1$, —$CONR^8$—$Q^2$, halogen, OH, —$SO_2R^8$, —$SO_2N(R^8)_2$, —$COR^8$, —$COOR^8$, —$N(R^8)_2$, —$NHCOR^8$, —$CONR^8OC_1$-$C_{10}$-alkyl-$Q^1$ and $CONR^8O$—$Q^2$,
$R^8$ in each case independently of one another denote hydrogen or a group selected from among optionally substituted $C_1$-$C_4$-alkyl, $C_2$-$C_4$-alkenyl, $C_2$-$C_4$-alkynyl and phenyl,
$Q^1$ denotes hydrogen, —$NHCOR^8$, or a group selected from among an optionally substituted —NH-aryl, —NH-heteroaryl, aryl, heteroaryl, $C_3$-$C_8$-cycloalkyl and heterocycloalkyl group,
$Q^2$ denotes hydrogen or a group selected from among an optionally substituted aryl, heteroaryl and $C_3$-$C_8$-cycloalkyl group,
and
n denotes 0, 1.

6. The compound according to claim 5,
wherein
$Q^1$, $Q^2$, n, $R^4$ to $R^8$ have the meanings specified,
$R^1$, $R^2$ which may be identical or different, denote hydrogen or a group selected from among methyl, ethyl, and propyl
or
$R^1$ and $R^2$ together represent cyclopropyl,
$R^3$ denotes hydrogen, or denotes optionally substituted $C_1$-$C_6$-alkyl or optionally substituted and/or bridged $C_3$-$C_{12}$-cycloalkyl, and
$R^{10}$ and $R^{11}$ denote hydrogen.

7. The compound according to claim 5,
wherein
$Q^1$, $Q^2$, n, $R^1$ to $R^4$, $R^6$ to $R^8$, $R^{10}$ and $R^{11}$ have the meanings specified,
and
$R^9$ which may be identical or different, denote hydrogen or a group selected from among halogen, $(C_1$-$C_4$-alkyl$)_2$N—, $CF_3$, $NH_2SO_2$—, —CONH—$C_6$-$C_{14}$-aryl, —CONH—$C_1$-$C_4$-alkyl-$C_6$-$C_{14}$-aryl and —O—$C_1$-$C_4$-alkyl.

8. A pharmaceutical preparation comprising as active substance one or more compounds of formula (I) according to claim 1 combined with one or more conventional excipients or carriers or both.

* * * * *